United States Patent [19]

Baumgartner

[11] Patent Number: 4,717,380

[45] Date of Patent: Jan. 5, 1988

[54] METHOD AND APPARATUS FOR MEDICALLY TREATING RECESSED BODY TISSUE

[76] Inventor: George C. Baumgartner, 41450 N. West Lake Ave., Antioch, Ill. 60002

[21] Appl. No.: 812,519

[22] Filed: Dec. 23, 1985

[51] Int. Cl.$^4$ .......................... A61M 31/00; A61B 1/06
[52] U.S. Cl. ...................................... 604/54; 128/753; 128/7
[58] Field of Search ................ 604/264, 54, 272, 274, 604/280; 128/311, 7, 749–754

[56] References Cited

U.S. PATENT DOCUMENTS

| | | | |
|---|---|---|---|
| 1,192,596 | 7/1916 | Albrecht | 604/274 |
| 2,097,039 | 10/1937 | Peterson | 604/272 |
| 2,568,207 | 9/1951 | Spicher | 604/272 |
| 3,051,176 | 8/1962 | Alberti | 604/264 |
| 3,509,880 | 5/1970 | Guttman | 604/272 |
| 3,595,217 | 7/1971 | Rheinfrank | 128/754 |
| 4,396,021 | 8/1983 | Baumgartner | 128/754 |
| 4,411,657 | 10/1983 | Galindo | 604/274 |
| 4,445,897 | 5/1984 | Ekbladh et al. | 604/280 |
| 4,461,280 | 7/1984 | Baumgartner | 604/51 |

*Primary Examiner*—C. Fred Rosenbaum
*Assistant Examiner*—Gene B. Kartchner
*Attorney, Agent, or Firm*—O'Neill & Bockelman

[57] ABSTRACT

A method and apparatus for medically treating recessed body tissues with medicament fluid. The invention comprehends aspirating the tissue to be treated prior to the introduction of the medicament fluid thereto so as to provide an improved delivery thereof. The apparatus includes a delivery tube having distributed openings at the distal end thereof and structure for selectively connecting either an aspirating syringe or a medical fluid delivery syringe at the opposite end. A support is provided having structure for permitting rotation of the tube about its longitudinal axis. A cystoscope is provided to permit the doctor to observe the location of the distal tip of the treatment apparatus for accurate location thereof in carrying out the fluid delivery.

4 Claims, 6 Drawing Figures

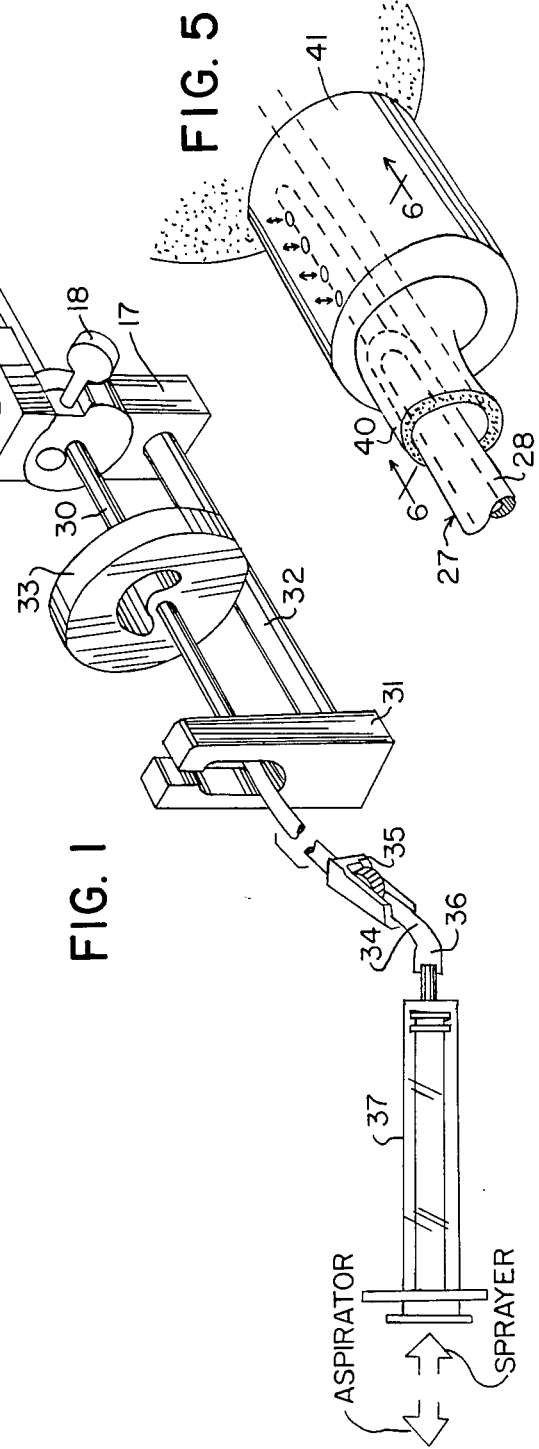

METHOD AND APPARATUS FOR MEDICALLY TREATING RECESSED BODY TISSUE

BACKGROUND OF THE INVENTION

1. Field of the Invention

This invention relates to surgical methods and apparatus and in particular to surgical methods and apparatus for providing fluid medicaments to recessed body tissues.

2. Description of the Background Art

It has long been conventional to provide fluid medicaments to recessed body tissues by means of a hypodermic syringe and needle. It has been common to provide fluid medication to recessed body tissues, such as male prostate gland, for treatment thereof.

One route for introducing the medication to the prostate gland has been transurethral, utilizing a catheter having a sharp distal tip for piercing the urethral wall adjacent the prostate gland and entering into the prostate for delivery of the fluid medication therethrough.

In my U.S. Pat. No. 4,461,280, apparatus was disclosed for use in delivering medication to the prostate gland. While that patent was primarily directed to means for taking biopsy samples, the apparatus was disclosed as being capable of providing medication to the prostate also.

However, it has been found that the use of the disclosed apparatus for delivering medication to the prostate was inefficient and did not fully assure the desired distribution of the medication in treating the prostate.

SUMMARY OF THE INVENTION

The present invention comprehends anna improved method and apparatus for treating recessed body tissue, such as a prostate gland, with medication fluid, which is extremely simple and economical while yet providing improved accuracy in the delivery to the desired portions of the tissue body.

More specifically, the invention comprehends the provision of such a medication-providing means having a delivery tube adapted to be inserted through the urethra to adjacent the prostate.

The tube end is provided with a sharp tip permitting it to be passed through the wall of the urethra and into the prostate. A cystoscope means is associated therewith to permit the doctor to observe the location of the delivery means and thereby assure proper delivery of the medicament fluid to the prostate as desired.

The end of the tube is provided with at least one radially opening aperture and, in the illustrated embodiment, a plurality of such apertures are aligned longitudinally of the tube end at preselected axially spaced intervals.

The distal end of the tube may be closed to provide all communication between the interior and exterior of the tube end through the apertures.

The invention further comprehends the provision of means for selectively coupling an aspirating syringe, or a fluid delivery syringe to the outer distal end of the delivery tube.

In the use of the apparatus, aspiration of the tissue body is first effected by utilization of the aspirator means sucking out fluids in interstitial cells from the tissue body and thereby permitting facilitated introduction of the medicament fluid.

The apparatus further includes means for observing the location of the end of the delivery tube, permitting the doctor to insert the delivery end of the tube into a plurality of desired locations in the prostate gland by successive insertion, withdrawal, and reinsertion steps.

Means are provided for controlling the angular disposition of the delivery tube about its longitudianl axis, as well as for providing for adjusted axial disposition thereof.

The method and apparatus of the present invention are extremely simple and economical, while yet providing for improved delivery of medicament fluids to recessed body tissues.

BRIEF DESCRIPTION OF THE DRAWING

Other features and advantages of the invention will be apparent from the following description taken in connection with the accompanying drawing wherein:

FIG. 1 is a fragmentary perspective view of a fluid medicament delivery apparatus embodying the invention;

FIG. 2 is a perspective view of a sheath portion of the cystoscopic means thereof;

FIG. 3 is a perspective view of an obturator portion thereof;

FIG. 4 is a fragmentary side elevation illustrating in greater detail the arrangement of the end of the treatment tube provided with apertures for effecting aspiration and medicament fluid delivery;

FIG. 5 is a fragmentary schematic perspective view illustrating the use of the apparatus in aspirating and/or delivering medicament fluid relative to a prostate gland of a patient; and FIG. 6 is a schematic view illustrating a distribution of the delivered medicament fluid transversely of the prostate gland.

BEST MODE FOR CARRYING OUT THE INVENTION

This invention comprises an improvement over applicant's earlier U.S. Pat. Nos. 4,396,021 and 4,461,280, which are directed to a surgical instrument and process utilizing means for extracting a biopsy sample from a prostrate, or similar body tissue, and for performing medical treatment thereof. The disclosures of said Letters Patent are incorporated by reference herein.

More specifically, a shown in FIG. 1 of the drawing herein, the apparatus of the present invention includes a cystoscope generally designated 10 having an obturator portion 11 removably received within a sheath 12. In the illustrated embodiment, the apparatus is adapted for inserting fluid medicament into the prostate and, thus, is adapted for insertion through the urethra of the patient to adjacent the prostate.

As illustrated in FIG. 1, sheath 12 defines a distal opening 13 and the end portion 14 of the sheath is configured to retain the tip 15 removably in position as the cystoscope is inserted through the urethra.

The opposite end 16 of the sheath 12 is mounted to a support member 17 provided with locking means generally designated 18. The locking mains comprises a member 19 on the sheath rotatable within the support 17. Member 19 is provided with a locking pin 20, which is selectively received in a slot 21 of the support for locking the obturator against rotation about its longitudinal axis when desired. Such rotation is effected manually by means of a gripping member 22 attached to the member 19, as shown in FIG. 1.

In use, the cystoscope 10 is firstly inserted as a unit through the urethra of the patient's penis. The end of the obturator is brought to adjacent the prostate, whereupon the obturator may be removed from the sheath and a conventional cystoscopic viewing means, generally designated 23, substituted.

The present invention is concerned with an improved method and apparatus for providing the desired deposition of medicament fluid in the tissue to be treated. As illustrated in FIGS. 1 and 4, the apparatus generally designated 24 includes, in addition to the cystoscope 10, and aspirator/fluid delivering means generally designated 25. Means 25 comprises means for controlledly delivering the medicament fluid in a novel and simple manner to the patient's tissue, such as the patient's prostate. The delivering apparatus 25 is associated with the cystoscope in the apparatus 24 in such a manner as to permit the doctor to view the area at the end of the cystoscope adjacent a distal end portion 26 of delivering apparatus 25. Apparatus 25 includes a tube 27 having an outer end 28 closed at 29. The opposite distal end 30 of the tube is connected to a knob 33 for controlled rotation and axial positioning of the tube from externally of the patient, i.e. outwardly of the support 17.

As further illustrated in FIG. 1, the support 17 may be provided with an outboard extension 31 mounted thereto by a suitable support rod 32.

Thus, the apparatus 10 may be inserted through the urethra of the patient to bring the distal end 28 of the tube 27 to adjacent the tissue to be treated, such as the patient's prostate, and the disposition thereof may be observed by the doctor through the cystoscope viewing means 23 for facilitated medicinal treatment of the prostate.

As further illustrated in FIG. 1, the outer end 30 of the tube is fixed to a rotatable knob 33, which may be manipulated to rotate the tube about the longitudal axis thereof, as desired. Outwardly of the knob, the tube defines a control portion 34 provided with a conventional clamp valve 35. The outer distal end 36 of the tube is provided with a removable syringe 37, which may comprise either an aspirating syringe, or a liquid delivery syringe, as desired.

As best seen in FIG. 4, the distal end 28 of the tube is provided with a plurality of axially spaced, longitudinally aligned openings 38 providing communication between the interior 39 of the tube and the exterior thereof. Thus, when the syringe 37 defines an aspirator syringe, suitable manipulation thereof causes aspiration of fluids from the surrounding tissue inwardly through the apertures 38 and the lumen 39 of the tube to the syringe. Thus, where the tissue to be treated comprises a patient's prostate gland, the aspiration may remove fluids and interstitial cells, providing an improved environment for reception of the desired medicament fluid.

Upon completion of the aspiration step, a medicament fluid syringe may be connected to the tube end 36 and operated to deliver the medicament fluid through the tube 27 and the apertures 38 thereof into the surrounding prostate gland tissue. Thus, as seen in FIG. 5, the distal end 28 of the tube 27 may be caused to pierce the urethral wall 40 adjacent the prostate gland 41 and enter into the prostate at desired cross-sectional locations, as illustrated in FIG. 6.

As illustrated in FIG. 6, delivery of medicament fluid may be at a plurality of different portions of the prostate about the central portion thereof and may be effected by sequentially inserting the sharp closed end 29 of the tube into the prostate of each of the indicated locations in FIG. 6. At each location, the above discussed steps of aspirating the tissue at that location and subsequent to delivery of the desired medicament fluid to that location may be effected. The movement of the sharp tip 29 of the tube end to the different locations may be effected without full withdrawal thereof through the urethra wall which, as shown in FIG. 5, is of sufficient flexibility to permit the sequential repositioning illustrated in FIG. 6 by simple stretching of the urethra with the tube end 28 maintained extending therethrough.

Rotation of the control knob 33 causes rotation of the tube about the longitudinal axis thereof in the support 17 and thereby directs the apertures 38 radially outwardly in each of the different positions illustrated in FIG. 6. As will be obvious to those skilled in the art, other directions of discharge of the medicament fluid from the tube end 38 may be utilized within the broad scope of the invention. As discussed above, the location of the distal end of the tube may be observed by the doctor through the cystoscope means 23 at all times to assure the desired distribution of delivery of the medicament fluid to the prostate, as desired.

It has been found that by providing for the aspiration of the tissue environment to be treated prior to the introduction of the medicament fluid thereto, substantially improved delivery of the desired medicament fluid to the tissue being treated is effected. The present invention contemplates a novel and simple apparatus for carrying out this highly desirable method of treatment, with minimum piercing and trauma of the tissue and the urethral wall.

In carrying out the treatment, the doctor may additionally utilize digital tactile determination of the location of the prostate and tube end through the patient's rectum within the broad scope of the invention.

In one method of carrying out the invention, the aspiration step may be effected as to all desired portions of the prostate and the medicament fluid delivery then effected to the aspirated prostate portions, whereby a single alternate connection of the aspirating syringe and medicament fluid providing syringe may be utilized in carrying out the medicament fluid delivery method.

The foregoing disclosure of specific embodiments if illustrative of the broad inventive concepts comprehended by the invention.

I claim:

1. The method of medically treating recessed body tissue such as that of a prostate gland, comprising the steps of:
    providing a tube defining a lumen and having an end portion having at least one opening communicating with said lumen;
    inserting said end portion of the tube through a patient's body into tissue to be treated recessed therein;
    aspirating fluid from the tissue outwardly through the opening and tube lumen;
    maintaining the tube end portion in the tissue following the aspirating step and delivering medicament fluid through the tube lumen and opening to the aspirated tissue; and
    withdrawing the tube from the tissue and body, viewing means being associated with said tube, said method further including the observation of the disposition of said tube end portion as it is inserted into the tissue to be treated.

2. The method of medically treating recessed body tissue such as that of a prostate gland, comprising the steps of:

provididing a tube defining a lumen and having an end portion having at least one opening communicating with said lumen;

inserting said end portion of the tube through a patient's body into tissue to be treated recessed therein;

aspirating fluid from the tissue outwardly through the opening and tube lumen;

maintaining the tube end portion in the tissue following the aspirating step and delivering medicament fluid through the tube lumen and opening to the aspirated tissue; and withdrawing the tube from the tissue and body, a plurality of openings being longitudinally aligned in said tube end portion, and said tube being selectively rotated about its longitudinal axis to direct said openings at a desired orientation with respect to said longitudinal axis within said tissue.

3. The method of medically treating recessed body tissue such as that of a prostate gland, comprising the steps of:

providing a tube defining a lumen and having an end portion having at least one opening communicating with said lumen;

inserting said end portion of the tube through a patient's body into tissue to be treated recessed therein;

aspirating fluid from the tissue outwardly through the opening and tube lumen;

maintaining the tube end portion in the tissue following the aspirating step and delivering medicament fluid through the tube lumen and opening to the aspirated tissue; and withdrawing the tube from the tissue and body, said tube end portion being selectively inserted into a first portion of the tissue, said aspiration and medicament delivery steps being sequentially effected, said tube end portion being withdrawn from said tissue while remaining recessed in the patient's body, and the tube end portion being inserted into another portion of the tissue and said aspirating, medicament delivering, and withdrawing steps being repeated to provide medicament to all desired portions of the recessed tissue.

4. Apparatus for medically treating recessed body tissue such as that of a prostate gland, comprising:

a tube defining a lumen and having an end portion having at least one opening communicating with said lumen;

means for inserting said end portion of the tube through a patient's body into tissue to be treated recessed therein;

means removably selectively associated with the tube for aspirating fluid from the tissue outwardly through the opening and tube lumen; and means removably selectively associated with the tube for delivering medicament fluid through the tube lumen and opening to the aspirated tissue; and cystoscopic means for viewing the tube end portion at the tissue.

* * * * *